United States Patent [19]

Ellis et al.

[11] Patent Number: 5,179,135
[45] Date of Patent: Jan. 12, 1993

[54] POLY(VINYLPHOSPHONIC ACID) GLASS IONOMER CEMENT

[75] Inventors: John Ellis, East Molesey; Alan D. Wilson, Liphook, both of England

[73] Assignee: National Research Development Corporation, London, England

[21] Appl. No.: 604,857

[22] Filed: Oct. 26, 1990

[30] Foreign Application Priority Data

Oct. 26, 1989 [GB] United Kingdom ............... 8924129

[51] Int. Cl.$^5$ ................... A61K 6/087; C08K 5/5317; C08K 3/22; C08K 3/40
[52] U.S. Cl. .................................. 523/116; 524/130; 524/430; 524/433; 524/492; 524/493; 524/494
[58] Field of Search ............... 523/116; 524/430, 433, 524/492, 493, 494, 130

[56] References Cited

U.S. PATENT DOCUMENTS 3,748,156 7/1973 Moore, Jr. .................. 106/38.3
4,647,600 3/1987 Kawahara et al. ............ 523/116
4,652,593 3/1987 Kawahara et al. ............ 523/116

FOREIGN PATENT DOCUMENTS 0340016 11/1989 European Pat. Off. .
WO79/00521 8/1979 PCT Int'l Appl. .
2182044A 5/1987 United Kingdom .

OTHER PUBLICATIONS

Research Disclosure No. 126, Oct. 1974, "A New Dental Restorative Material . . . " pp. 50–51.
Chemical Abstracts, vol. 93, No. 12, Sep. 1980, p. 345, Abstract No. 120375t, Columbus, Ohio, Crisp et al. Abstract for JP 57126407.

Primary Examiner—Paul R. Michl
Assistant Examiner—Peter Szekely
Attorney, Agent, or Firm—Nixon & Vanderhye

[57] ABSTRACT

A glass ionomer cement composition comprises poly(vinyl phosphonic acid) dissolved in its own mass of water; and (in treble the total mass of the solution) a powder, being glass or MgO or a cement. The powder has to be deactivated so that the setting reaction with the acid is not too fast, and this is achieved either by a raised Si:Al ratio or by heat-treating. The glass contains heavy ions such as La, Ba or Sr.

14 Claims, No Drawings

POLY(VINYLPHOSPHONIC ACID) GLASS IONOMER CEMENT

This invention relates to a glass ionomer cement made using poly(vinyl phosphonic acid). This cement may find application for specialised surgical purposes, such as dental fillings and cements and as splint bandage materials.

Glass-ionomer cements were developed in the early 1970's to meet requirements for a more acid-resistant filling material to replace dental silicate cement, formerly in widespread use. Those cements, now called glass polyalkenoate cements in ISO nomenclature, set by an acid-base reaction between an acid-decomposable glass powder, which acts as a base, and a concentrated solution (typically 50%) of poly(acrylic acid)

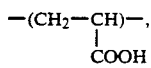

or its copolymers with methacrylic or itaconic acids. On mixing the glass and the acid, cations ($Ca^{2+}$ and $Al^{3+}$), released from the glass, cross-link the polyacid chains. A metal polysalt is formed which acts as a binding matrix for the partially reacted glass particles. Thus glass polyalkenoate cements are composite materials, consisting of a glassy filler embedded in an insoluble metal polyacrylate matrix.

Those cements are unusual in being adherent to tooth dentine and enamel, providing excellent seals when used as filling materials. Thus, they prevent ingress of fluid and debris into the tooth at the restorative/cavity wall margin, and so prevent secondary tooth decay. They are however susceptible, before they are fully set, to contamination by moisture. They are also not sufficiently translucent to match tooth enamel optically

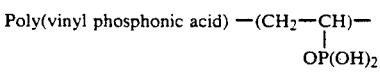

is a stronger acid than poly(acrylic acid), and hence offers the possibility of producing stronger cements, with the adhesion characteristic of existing cements. However, it has not proved easy to synthesise, nor can it be simply used as a direct replacement for poly(acrylic acid).

According to the present invention, a cement composition comprises an intimately blended mixture of a water-containing liquid, a cation-catalysed cross-linkable polymeric acid containing on average one phosphonic acid group per one to three backbone carbon atoms, such as poly(vinyl phosphonic acid) PVPA optionally containing poly(acrylic acid), and a cation-leachable surgically acceptable glass powder containing Si and Al in the mole proportions 0.6–0.2:1 if previously heat-treated, otherwise exceeding 1.6:1, in the proportions $(1-x)$g phosphonic acid e.g. PVPA: 1-5 g glass: x g liquid, where x is from 0.3–0.7, characterised in that the glass contains at least 10% by weight (as the oxide or salt) of a polyvalent metal of atomic number exceeding 37. The solvent is preferably aqueous, i.e. water, and preferably dissolves the acid, the glass being kept separate until use. However, the acid may be dried and mixed with the glass: the invention extends to this mixture, which is preferably packed in a sealed capsule (PVPA being hygroscopic) and which is made into cement by adding the solvent. The said polyvalent metal oxide is for example strontium oxide SrO, barium oxide BaO or lanthanum oxide LaO or the corresponding fluorides or a mixture (of metals and/or of oxides/salts) may be used.

The invention extends to a pack comprising two pastes which when mixed form a cement composition as set forth above; the first paste may be the acid(s) plus water, and the second paste may be the glass powder suspended in aqueous thickening agent e.g. methylcellulose. If the two pastes have been formulated to appropriate concentrations, one could in use squeeze out equal lengths of paste from two tubes, or scoop out equal numbers of spoonfuls from two tubs, as an easy way to ensure that the mixture is of the correct composition.

The composition may further contain acid-neutralising agents such as zinc oxide or agents such as aluminium phosphate or both, in a total amount of up to 10% by mass based on the acid solution, and/or complexing agents such as phosphonic-acid-based materials.

The glass powder preferably consists of particles substantially all of which are smaller than 100 microns, preferably smaller than 60 microns. Preferably the glass powder has been heat-treated at least 400° C. (preferably 450°–600° C.) for at least 40 minutes (preferably at least 55 minutes). The Si:Al range of 0.6–2:1 yields an opaque product, which may be acceptable in appropriate cases. The glass may be washed in a dilute acid such as acetic acid, preferably in a y% concentration for z hours where yz<4, preferably ≦2.

The invention also extends to a pack comprising the components of the cement composition set forth above, so packed that when unpacked and mixed they form the cement.

Poly (vinyl phosphonic acid).

Poly(vinyl phosphonic acid), PVPA, can be prepared by a free radical polymerisation in an inert solvent, using or example vinyl phosphonic acid monomer. The polymer is a light brown very hygroscopic solid, which dissolves readily in water to give solutions of up to 80–85% by weight. The solutions show good long term stability with no evidence of gelling. A 50% solution typically has a viscosity of 0.8–0.9 cP.

Properties of PVPA Cements

The apparent pKa value of poly(vinyl phosphonic acid) is not known but it is certain to be a stronger acid than poly(acrylic acid), apparent pKa 5–6, since its dibasic monomer, vinyl phosphonic acid, has pKa values of 2 and 8 compared with a pKa value of 4.25 for acrylic acid. It is expected therefore that the aforementioned cross-linking cations released from glass powder ($Ca^{2+}$ and $Al^{3+}$) would form stronger associations between the polyacid chains, leading to stronger cements.

In practice, however, cement formation with the glass types used in current glass-ionomer cements is difficult when PVPA is used in place of PAA. For example, a glass which has a setting time of 3–4 minutes with PAA solution will set in probably less than 45 seconds with PVPA solutions. It thus proved necessary to modify the cement system to allow a reasonable working and setting time for the cement paste, by: i) using glasses with a different formulation which allows adequate working time, or by deactivating reactive glasses; ii) partially neutralising the PVPA solution, so reducing its reactivity, and iii) use of additives, such as complexing agents, in the liquid; these are believed to tie up cations as they are released from the glass and delay the setting of the cement.

Using a cement according to the invention as above, cements with setting time of about 5 minutes can be obtained, which is comparable with existing glass-ionomer cements (5–20 minutes).

Dental Requirements

1. Adhesion.

Adhesion of a dental restorative material to the tooth substrate is of prime importance. The dental silicate cement (now no longer used since inadequately acid-resistant), typical of phosphoric acid based cements, did not adhere to the tooth enamel and as a consequence fluid and debris could leak into the tooth at the edge of the filling, possibly resulting in secondary tooth decay. An adhesive filling material will (in contrast) effectively seal this edge. In addition, with non-adherent restoratives, the filling needs to be mechanically keyed into the tooth by undercutting, with the loss of excessive sound tooth material. This is not necessary with adhesive materials.

2. Biocompatibility and toxicity.

Glass-ionomer cements are known to be compatible with the oral tissues and do not irritate the dental pulp as phosphoric acid based cements do. This improvement is attributable to the very low diffusion of bulky polymer molecules through the dental tubinals leading to the pulp. Cements based on PVPA are expected to be equally bland, and like PAA cements they also show very small temperature rises on setting.

Current glass-ionomer cements show resistance to acid attack and to staining and PVPA-based cements are expected to show similar properties.

The toxicity of the PVPA starting material vinyl phosphonyl dichloride is known to be high, but this is converted 100% to vinyl phosphonic acid monomer and polymer. The toxicity of the VPA monomer is not known, but its complete removal from the polymer solution prior to cement formation is readily possible as described later. As a matter of interest, the monomer has been found to form insoluble cements with certain metal oxides, and would not therefore be expected to be leachable even if present in the initial polyacid solution.

3. Translucency.

If a restorative material is to be successfully used as an anterior filling material, then its translucency should match that of the surrounding tooth material, to give a "live" appearance. Dentine has an opacity of 0.51–0.93 ($C_{0.70}$ value, test disc thickness 1 mm, two discs compared for strength of reflected light when one sits on a white (reflectivity 0.70) and the other on a black background), while enamel has an opacity of 0.21–0.67. The opacity of glass-ionomer restorative material is affected by the refractive indices of the glass particles and of the gel matrix; a close match of the refractive indices results in a low-opacity cement.

The British Standard for glass-ionomer cements quotes limits for the opacity of cements as 0.35–0.90 ($C_{0.70}$ value), and typical values are 0.65–0.75 for filling cements, above the range for enamel. Dental silicate cements had a much lower opacity (B.S. opacity value 0.35–0.55, typically 0.45–0.55), but these are no longer in use. Measurement of the opacity of a cement prepared from PVPA and a modified dental silicate glass gave a $C_{0.70}$ value of 0.40–0.46 compared with 0.5–0.6 for a cement prepared from the same glass and PAA of a similar molecular weight as the PVPA. Such low opacity indicates that aesthetic anterior fillings should be possible using PVPA cements.

The invention will now be described by way of example.

Part 1

This part describes the preparation of a polymer of vinyl phosphonic acid from vinyl phosphonyl dichloride (VPDC). VPDC is dissolved in an equal volume of 1,1,1-trichloroethane and to this solution is added the initiator, azo-bis-isobutyronitrile, at a level of 3% by weight of the monomer. The mixture is heated under nitrogen, with stirring, in a flask equipped with a reflux condenser to a temperature of 70° C. for two hours. Heating is by means of a water bath, surrounding the flask, to maintain adequate temperature control. If the entire polymerisation (18 hours) were carried out at 70° C., the yield would be 50–60%. Instead, after two hours at 70° C., the temperature is lowered to 40°–45° C. and maintained at this temperature for a further 16–18 hours, whereby the yield is increased to 85–90%.

A viscous, orange-brown solution results, which is a solution of the crude polymer of vinyl phosphonyl dichloride. This is then hydrolysed by pouring slowly into a large volume of chilled water with stirring, removing the bulk of the HCl gas as it is formed by means of a vacuum. The hydrolysed product is then concentrated, and the excess organic solvent removed by vacuum distillation or by means of a rotary evaporator.

Analysis of the product typically shows it to contain 85–90% of the desired PVPA—poly(vinyl phosphonic acid), a solid, together with some 10–15% residual monomer.

Part 2

This part describes the purification of the product prepared as described in Part 1. The PVPA must first be isolated by removing the water introduced by the hydrolysis, using a rotary evaporator or similar. The resulting solid is then dissolved in an equal or lesser weight of ethanol (other alcohols can be used), with gentle warming as necessary. The solution is then poured slowly into a large excess of a non-solvent, such as ethyl acetate, with stirring. A white precipitate forms, which is isolated from the solvent mixture, and contains some 5% of residual monomer. Repeating the dissolution in ethanol and the precipitation with ethyl acetate leaves no residual monomer detectable by P-31 NMR spectroscopy.

Pure PVPA is a hygroscopic, off-white solid. It is readily soluble in water up to concentrations greater than 80% by weight when prepared as described. The viscosity of an infinitely dilute solution (intrinsic viscosity), obtained by the extrapolation of the measured viscosities of solutions of concentrations 1, 2, 3 g/100 ml (sodium salt of PVPA in 1M NaCl) is 0.08 ml/g, suggesting a polymer of low molecular weight, probably in the range 3000–5000.

Part 3

This part envisages the cement-forming properties of aqueous solutions of poly(vinyl phosphonic acid) with barium or strontium (or other metal of atomic number exceeding 37, excluding Cu, Co, Sn, Bi, Pb, Hg, Cd, Y, La and Mo) oxide powders, i.e. not with glass as such.

In all cases a 50% by weight aqueous solution of poly(vinyl phosphonic acid), prepared as described in Parts 1 and 2, is used as the cement-forming liquid. The liquid and a powdered metal oxide are mixed together on a glass block with a metal spatula at a g powder: ml liquid ratio which gives a homogeneous paste, and which is from 1:1 to 5:1 depending on the reactivity and bulk density of the metal oxide powder.

Parts 4–11 are not according to the invention but are included to indicate the scope of possible variations and to indicate the techniques.

Part 4

This part illustrates the properties of a typical cement prepared from an aqueous solution of poly(vinyl phosphonic acid) and an ion-leachable aluminosilicate glass. The polyacid solution used is 50% m/m. The glass is prepared by mixing together 437 parts by weight silica, 230 parts by weight alumina, 129 parts by weight calcium fluoride, 175 parts by weight cryolite and 29 parts by weight aluminium phosphate and heating to 1300° C. for 75 minutes. The melt is cooled rapidly by pouring into water. The resulting glass is ground and sieved, and the fraction of particle size less than 45 microns used to prepare the cement. Before use, the glass powder is deactivated by heating in a furnace at 450° C. for 90 minutes.

Part 4A

The setting properties of the poly(vinyl phosphonic acid) cement of Part 4 are compared with commercial glass ionomer cements containing poly(acrylic acid) or similar. Setting times were determined using a 453 g Gillmore needle. Working times and setting rate were determined from Wilson rheograms.

|  | Cement | | |
| --- | --- | --- | --- |
|  | PVPA | Fuji Type II | DeTrey ASPA |
| g powder/ml liquid | 3.0 | 2.75 | 3.0 |
| Working time/ mins, 23° C. | 0.6 | 2.7 | 2.4 |
| Setting time/ mins, 23° C. | 2.0 | — | — |
| Setting time/ mins, 37° C. | 1.33 | 7.5 | 4.25 |
| Setting rate/ mins, 23° C. | 71.6 | — | — |

The PVPA coment could be made with glass acetic-acid washed for 1 or 2 hours, acid concentration being 1% or 2%. All combinations extended the working time and slowed the setting rate, which could be useful, but 2 hours/2% did so rather strongly.

Part 4B

The mechanical properties of the poly(vinyl phosphonic acid) cement were compared with commercial glass ionomer cements. The cements were mixed at the powder/liquid ratios given in Part 4A. Compressive strengths were determined on cylindrical specimens (12 mm length, 6 mm diameter), after storage for 24 hours.

Flexural strength was determined using specimens of dimensions 25×3×3 mm.

|  | Cement | | |
| --- | --- | --- | --- |
|  | PVPA | Fuji Type II | DeTrey ASPA |
| Compressive strength/MPa | 75 | 174 | 140 |
| Flexural strength/MPa | 10 | 8.9 | 9.8 |

Part 4C

This Part illustrates the translucency of the poly(vinyl phosphonic acid) cement. The cement paste is placed in a brass mould, such as will give a cement disc of diameter 2.0 cm and thickness 0.1 cm. The mould is closed with steel plates and the cement allowed to set. The cement disc is removed from the mould after one hour, and subsequently stored in water for a further 24 hours. The opacity of this cement disc, when measured on a Hunterlab D25A-9 Tristimulus Colorimeter is superior to that of a similar cement prepared using poly(acrylic acid) as the cement forming liquid, and compares favourably with the opacity of a similarly prepared commercial dental silicate cements (DSC) and glass ionomer cements (GI). The $C_{0.70}$ opacities obtained for the cements are given in the Table.

| cement | g powder:ml liquid | opacity % |
| --- | --- | --- |
| PVPA | 2.2:1 | 44 |
| PAA | 2.2:1 | 55 |
|  | 3.5:1 | 60 |
| DSC(1) | 3.5:1 | 47 |
| DSC(2) | 3.5:1 | 45 |
| GI(1) | 2.75:1 | 69 |
| GI(2) | 3.0:1 | 85 |

PVPA Poly(vinyl phosphonic acid)
PAA Poly(acrylic acid)
DSC(1) "BioTrey" dental silicate cement
DSC(1) "Achatit"
GI(1) "Fuji Ionomer Type II"
GI(2) "DeTrey ASPA"

Part 4D

This Part illustrates the rapid development of water stability of cements prepared from poly(vinyl phosphonic acid), and compares this feature with similar cements prepared from poly(acrylic acid) and with commercial glass ionomer cements. Thus, a specimen is prepared by placing the cement paste (powder/liquid ratio 3 g: 1 ml) in a brass mould such as to give set cement disc of diameter 2 cm and thickness 0.2 cm. A length of unwaxed dental floss is placed in the cement paste, by which to suspend the set cement disc. After being allowed to set for 7 minutes or 1 hour, as required, the disc is removed from the mould, and immediately suspended in a tared weighing bottle containing a fixed volume of water. After 24 hours in water, the disc is removed, and the water evaporated, leaving the residue leached from the cement disc. The water stability of the cement is thus determined from the difference in weight of the bottle and the weight of the cement disc.

The water stabilities of cements thus determined are given in the Table.

|                                  | Cement |              |              |
| -------------------------------- | ------ | ------------ | ------------ |
|                                  | PVPA   | Fuji Type II | DeTrey ASPA  |
| Water-leachable material, 7 min (%) | 0.50 | 1.90       | 2.10         |
| Water-leachable material, 1 hr (%)  | <0.05 | 0.70       | 0.30         |

Part 5

This example describes the cement forming properties of a range of glass powders based on that described in Part 4, and prepared by altering the pre-fired composition of the glass. Thus the effect of altering the amount of aluminium phosphate (5A–5D), the Si/Al ratio (5E–5H), and the amount of fluoride (calcium fluoride) (5J–5M) in the glass is described. The glass compositions are listed below as parts by weight.

The setting times of cements prepared from these glass powders are given, measured at 23°–24° C. and ambient humidity. Deactivation of the glass powders is achieved by heating at 450° C. for 90 minutes.

| glass no. | SiO$_2$ | Al$_2$O$_3$ | CaF$_2$ | Na$_3$AlF$_6$ | AlPO$_4$ | setting time (secs) unheated | heated |
| --- | --- | --- | --- | --- | --- | --- | --- |
| 5A | 416 | 219 | 123 | 166 | 144 | <10 | 50 |
| 5B | 416 | 219 | 123 | 166 | 171 | <10 | 40 |
| 5C | 416 | 219 | 123 | 166 | 29  | <20 | 70 |
| 5D | 416 | 219 | 123 | 166 | 0   | <10 | 130 |
| 5E | 499 | 219 | 123 | 166 | 57  | <15 | 225 |
| 5F | 582 | 219 | 123 | 166 | 57  | <20 | 450 |
| 5G | 332 | 219 | 123 | 166 | 57  | <10 | <15 |
| 5H | 249 | 219 | 123 | 166 | 57  | <10 | <15 |
| 5J | 416 | 219 | 148 | 166 | 57  | <15 | 80 |
| 5K | 416 | 219 | 172 | 166 | 57  | <15 | 60 |
| 5L | 416 | 219 | 98  | 166 | 57  | <15 | 50 |
| 5M | 416 | 219 | 74  | 166 | 57  | 20  | 70 |

Part 6

This Part describes the preparation of a cement from an ion-leachable glass and an aqueous solution of PVPA. A calcium fluoroaluminosilicate glass is prepared by mixing together 67 parts by weight of silica, 100 parts by weight of alumina and 100 parts by weight of calcium fluoride, and heating to a temperature of 1300 degC for 90 mins. The melt is rapidly cooled by pouring into cold water, and the resulting glass-ceramic crushed and sieved so as to collect the fraction of particle size less than 45 microns. The cement is prepared using a 50% by weight solution of poly(vinyl phosphonic acid) at a p/l ratio of 3:1. The resulting cement-forming reaction is very vigorous, and a hard, dense cement-like mass results in less than 10 seconds.

The glass powder can be deactivated by heating to 600° C. for at least 1 hour. When mixed with the poly(vinyl phosphonic acid) solution, this deactivated glass powder gives a setting time (at 23-24 degC) of 105 seconds. The compressive and flexural strengths of this cement are given below and are compared with the compressive strengths of similar cements prepared using poly(acrylic acid) as the cement forming liquid, and the same (unheated) glass powder.

| Cement liquid | Compressive strength/MPa dry | 100% RH | Flexural strength/MPa 100% RH |
| --- | --- | --- | --- |
| PVPA   | 67 | 73 | 11.6 |
| PAA(1) | 90 | 90 | —    |
| PAA(2) | 40 | 40 | —    |

(1) Allied Colloids "Versicol E5" 50% w/w
(2) Aldrich Co. PAA MW 2000 50% w/w

Part 7

This Part illustrates the effect of altering the Si/Al ratio on the cement properties of the glass type described in Part 6. Thus a series of glass powders was prepared as described, with Si/Al mole ratios from 2.5:1 to 0.23:1, by altering the amount of silica in the pre-fired mixture. This is the ratio by number of the silicon atoms to the aluminium atoms present. Cements were mixed at 2.5 g powder: 1 ml liquid and setting times measured at 23°–24° C. The Table also shows the effect of heating to 600° C. on the reactivity of the glasses.

| Glass no. | Si/Al mole ratio | Relative masses in prefired mixture SiO$_2$ | Al$_2$O$_3$ | CaF$_2$ | Setting time (secs) unheated | heated to 600° C. for 6 hours |
| --- | --- | --- | --- | --- | --- | --- |
| 7A | 2.0:1  | 300 | 100 | 100 | 975 | —    |
| 7B | 2.2:1  | 266 | 100 | 100 | 340 | 1500 |
| 7C | 1.94:1 | 233 | 100 | 100 | 190 | —    |
| 7D | 1.67:1 | 200 | 100 | 100 | 120 | 320  |
| 7E | 1.11:1 | 133 | 100 | 100 | <5  | <15  |
| 7F | 0.78:1 | 94  | 100 | 100 | <5  | <15  |
| 7G | 0.56:1 | 67  | 100 | 100 | <15 | 105  |
| 7H | 0.42:1 | 50  | 100 | 100 | 70  | 130  |
| 7I | 0.23:1 | 27  | 100 | 100 | 205 | 320  |

Glasses 7G, 7H and 7I after heating were partly crystallised, so that the "real" (amorphous) glass apart from the crystals would have had a composition deviating from the overall nominal composition. That actual composition was not determined. It may account for the reversal in the trend of setting times.

Similarly the Si/Al ratio has an effect on the physical properties of the set cements, as shown in the Table below. The glass powders for making the last three cements were heat-treated at 600° C. for 6 hours.

| Si/Al ratio | Compressive strength/MPa dry | 100% RH | Flexural strength/MPa 100% RH | g powder/ml liquid |
| --- | --- | --- | --- | --- |
| 2.50 | 31.6 | 16.4 | 3.3  | 2.5 |
| 2.22 | 27.6 | 22.9 | —    | 2.5 |
| 1.67 | 24.6 | 23.5 | —    | 2.5 |
| 1.67 | 31.6 | 32.2 | 4.2  | 3.0 |
| 0.56 | 67.0 | 73.0 | 11.6 | 3.0 |
| 0.42 | 69.0 | 65.0 | 7.7  | 3.0 |

Part 8

This Part illustrates the effect of altering the fluoride content of the type of glass described in Part 4. Thus cements were prepared as described, using glass powders of constant Si/Al mole ratio (viz. 1.48:1), but with varying amounts of fluoride. The effect on the setting time of such cements (mixed at 2.5 g powder: 1 ml liquid) is given in the Table.

| glass no. | Relative masses prefiring SiO₂ | Al₂O₃ | CaF₂ | mol % F | setting time |
|---|---|---|---|---|---|
| 8A | 175 | 100 | 553 | 40.6 | 465 sec |
| 8B | 175 | 100 | 240 | 26.9 | 95 sec |
| 8C | 175 | 100 | 110 | 15.8 | <10 sec |

Fluoride acts as a fluxing agent, making the glass easier to work (as may be imagined - in glass 8A, fluorine atoms are 40.6% by number of the whole, all other species of atom added together being only 59.4%). Fluoride makes the glass more susceptible to acid attack, and it moderates the setting reaction.

Increasing the Ca:Al ratio generally decreases the setting time if no other factors are varied.

Part 9

This Part describes the effect of the incorporation of aluminium phosphate, zinc oxide and mixtures thereof in the aqueous poly(vinylphosphonic acid) solution, on the working time and the setting rate of the glass described in Example 4. A Wilson rheometer is used to determine these data on cements (3 g powder: 1 ml liquid) mixed at 23°–24° C. The glass powder was deactivated by heat-treating at 450° C. for 90 minutes before use.

| Additive | | Working time (mins) | Setting speed (arbitrary units) |
|---|---|---|---|
| PVPA | | 0.6 | 78.3 |
| 2% | ZnO | 0.6 | 110.4 |
| 5% | | 0.5 | 116.8 |
| 10% | | 0.85 | 153.7 |
| 2% | AlPO₄ | 0.45 | 128.9 |
| 5% | | 0.5 | 157.6 |
| 10% | | | |
| 1 + 1% | ZnO + | 0.5 | 144.2 |
| 2.5 + 2.5% | AlPO₄ | 0.7 | 118.0 |

Percentages are by mass on the liquid component.

Part 10

This Part describes the effect of adding chelating compounds on the working properties of the cements described above. The additives were incorporated into the polymer solution so as to give a final solution containing 45% m/m PVPA and 5% m/m (unless otherwise stated) of the additive. A number of additives were tried: all were phosphonic acids manufactured by Monsanto Co. under the trade mame "Dequest". The Dequests tried and found to be useful were:
Dequest 2000: aminotris(methyl phosphonic acid)
Dequest 2010: hydroxyethyl-diphosphonic acid
Dequest 2060: diethylenetriamine-penta(methylene-phosphonic acid)

The modified PVPA solution was mixed with two types of glass (Parts 4 and 6 above, 3 g powder: 1 ml liquid. The setting time was determined with a 453 g Gillmore needle at 23°–24° C. and ambient humidity (55%). The effect of Dequests on the setting of cements prepared from untreated and heat treated glasses was studied, and the results shown below. (The effect of Dequests on the compressive and flexural strengths of the cements of Part 7 was studied and found to be insignificant).

An estimate of the working time (manipulability) of each of the cements was made by examination of the rheograms obtained using a Wilson rheometer for each of the cements.

TABLE 1

| liquid | glass | setting time/secs | working time/secs |
|---|---|---|---|
| PVPA | Part 4* | 80 | 20 |
| PVPA/D2000 | Part 4* | 110 | 20 |
| PVPA/D2010 | Part 4* | 95 | 40 |
| PVPA/D2060 | Part 4* | 80 | 20 |
| PVPA | Part 4 | 140 | 35 |
| PVPA/D2000 | Part 4 | 140 | 70 |
| PVPA/D2010 | Part 4 | 190 | 90 |
| PVPA/D2060 | Part 4 | 150 | 50 |

*but not deactivated by heating before use.

TABLE 2

| liquid | glass | setting time/secs | working time/secs | compressive strength (MPa) |
|---|---|---|---|---|
| PVPA | Part 6 | <20 | <10 | |
| PVPA/D2000 | Part 6 | 50 | 30 | |
| PVPA/D2010 | Part 6 | 40 | 20 | |
| PVPA/D2060 | Part 6 | <30 | <20 | |
| PVPA | Part 6* | 90 | 50 | |
| PVPA/D2000 (2%) | Part 6* | 120 | 70 | 75 |
| PVPA/D2000 | Part 6* | 130 | 85–90 | 81 |
| PVPA/D2000 (10%) | Part 6* | 190 | 100 | 109 |
| PVPA/D2010 (2%) | Part 6* | 100 | 50 | 53 |
| PVPA/D2010 | Part 6* | 140 | 70 | 53 |
| PVPA/D2010 (10%) | Part 6* | 180 | 70 | 76 |
| PVPA/D2060 | Part 6* | 120 | 80 | |

Comparison of PVPA and PAA cements.

| | cement | | |
|---|---|---|---|
| | PVPA Part 4 | Fuji Type II | DeTrey ASPA |
| g powder per ml liquid | 3.0 | 2.75 | 3.0 |
| WT (mins, 23° C.) | 0.6 | 2.7 | 2.4 |
| ST (mins, 37° C.) | 1.3 | 3.75 | 4.25 |
| ST (mins, 23° C.) | 2.0 | | |
| CS (MPa, 24 Hr) | 75 | 174 | 140 |
| FS (MPa, 24 Hr) | 10 | 8.9 | 9.8 |
| Sol | | | |
| 7 mins | 0.50 | 1.90 | 2.10 |
| 1 hour | >0.05 | 0.70 | 0.30 |
| Opacity (C₀.₇₀ value) | 0.44 | 0.69 | 0.85 |

But not deactivated.
*Deactivated by heat-treatment at 600° C. for 90 minutes.
WT = Working time (measured by 28 g needle leaving no visible impression)
ST = Setting Time (measured by 453 g needle leaving no visible impression)
CS = Compressive Strength
FS = Flexural Strength
Sol = % dissolved when immersed at stated time after mixing, for 24 hours in 37° C. water.

An ideal dental filling material will have a 37° C. setting time of 3–6 minutes from starting the mixing or 2–5 minutes from completing the mixing (itself done at 23° C.), following a relatively leisurely working time.

Part 11

This part describes the cement formed between an aqueous solution of poly(vinyl phosphonic acid) and a tin cermet. The tin cermet was prepared by mixing glass powder (as described in Part 6, but ground to 18 μm) with tin powder (Goodfellow Metals, sieved to <45 μm) in equal volumes (1:4 by weight). The mixture was compressed to form a 2.5 cm diameter disc under a pressure of 20 tonnes. The discs were then sintered in a vacuum furnace at 210° C. for 30 minutes before being ground to a powder and passed through a 15 μm sieve.

A cement was prepared by mixing a 50% by mass solution of PVPA with the cermet material prepared as described above, in the ratio 5 g powder: 1 ml liquid.

The cement was water stable on setting. It had the following properties:

| | |
|---|---|
| working time/secs (23° C.) | 260 |
| setting time/secs (23° C.) | 600 (approx) |
| compressive strength/MPa (100% RH, 4 days) | 36.2 |

EXAMPLES OF PASTES

Cements prepared by mixing two pastes, as opposed to a powder and liquid, have the advantage of ease of measuring and give an easier mix. Solutions of PVPA at concentrations of 80% m/m (by mass) can be prepared, these being viscous liquids. The possibility of using such concentrated solutions as part of a two paste glass ionomer type cement was investigated, the other paste being a glass powder suspended in water and some dispersing aid.

Materials

80% m/m PVPA solution was used as one component of the cement. The glass paste was prepared by mixing G5 (i.e. the glass of Part 4 above) with sufficient water such that when this paste was mixed with the PVPA solution, a 50% m/m solution of PVPA in water resulted. In addition, various dispersing aids were added to the glass paste to prevent drying out. Sufficient glass to give an approximately 3:1, or more usually 5:1, p/l ratio with the 50% PVPA solution was used. A density of 1.0 g cm$^{-3}$ was assumed for a 50% PVPA solution.

The dispersing aids used in this study were "Cellosolve" (i.e. ethoxyethanol), Tween 80 (a non-ionic surfactant) and Dequest 2010 (explained in Part 10). The composition of the glass pastes are given in Table 3.

The G5 glass was used both unheated and heat treated (450° C. 90 mins) where marked with asterisk (G5*).

Results and Discussion

Firstly, a cement was prepared from 80% PVPA and glass powder. A maximum p/l ratio of 1:1 was possible, giving a stiff but workable paste (Paste O). This cement had a very long setting time, and remained soft and pliable at >1 hr. The poor setting characteristics of this cement confirmed that there is a reaction to occur. Generally cements are prepared from 50-60% m/m PVPA solutions.

The setting behaviour of the cements prepared from the glass pastes of Table 1 are shown in Table 5. The compressive strengths of the cements are shown in Table 2. All of the cements when mixed as two pastes gave a homogenous paste within 10 seconds, except paste no. 6. In this case the unheated glass reacted with D2010 in the glass paste, forming a friable solid. When mixed with the PVPA solution the resulting cement set very rapidly (<20 seconds). With the heat deactivated glass (e.g. in Pastes 4 and 5) there was no reaction noticed between preparing the glass paste and forming the cement from it, generally about 5-10 minutes, although storage of such a paste may have shown similar problems to that observed for Paste 6. By adding the D2010 to the PVPA solution however, (Paste 7), such problems were overcome. This cement (Paste 7) used non-deactivated G5, and consequently had a working time similar to that obtained for a standard powder-liquid mix. However, the p/l ratio of this cement was almost double that which could be achieved with a normal mix.

In general, mixing cements from two pastes gave a homogeneous mix of higher p/l ratio than could be achieved by mixing a powder and liquid. The working times of the cement pastes were also increased, especially when using cellosolve in the glass paste. However, the disadvantage with all of the cements was their low strength when compared with the normal powder-liquid cements, Table 2. Although the incorporation of D2010 did increase the strength of the cements, it was not able to fully compensate for the weakening effect of the other additives (i.e. cellosolve or Tween 80). Typically, a cement prepared from 50% PVPA, containing 5% D2010, and G5*, at a p/l ratio of 3:1 has a compressive strength of 85-90 MPa.

The two paste cements may therefore be limited in their applications to temporary restoratives, for example. Further work is required to identify other dispersing aid, which might have less effect on the strength of the resulting cements.

TABLE 3

Composition of Glass Pastes.

| Paste no. | glass | water | dispersing aid | nominal p/l |
|---|---|---|---|---|
| 1 | 0.36 g G5* | 0.09 g | 3 drops cellosolve | 3:1 |
| 2 | 0.60 g G5* | 0.09 g | 6 drops cellosolve | 5:1 |
| 3 | 0.60 g G5* | 0.09 g | 2 drops Tween 80 | 5:1 |
| 4 | 0.60 g G5* | 0.09 g | 3 drops D2010 | 5:1 |
| 5 | 0.60 g G5* | 0.07 g | 1 drop D2010 1 drop Tween 80 | 5:1 |
| 6 | 0.60 g G5 | 0.07 g | 1 drop D2010 1 drop Tween 80 | 5:1 |
| 7 | 0.60 g G5 | 0.07 g | 2 drops Tween 80 (1 drop D2010 added to PVPA solution) | 5:1 |

All cements were prepared by mixing the glass pastes with 0.15 g of 80% m/m PVPA solution.

TABLE 4

Compressive strength of Two-Paste Cements.

| Glass paste No. | Compressive strength MPa |
|---|---|
| 1 | 10.5 |
| 2 | 11.2 |
| 3 | 9.8 |
| 4 | 43.8 |
| 5 | 30.6 |
| 7 | 37.1 |

Compressive strengths were measured in cements 24 hours old, stored at 37° C., 100% RH.

TABLE 5

| Paste No. | Setting characteristics |
|---|---|
| 0 | Steady but very slow (>> 1 hour) |
| 1 | No setting for 5 minutes, rapid setting 6-11 minutes, substantially fully set by 15 minutes. |
| 2 | No setting for 6 minutes, rapid setting 7-15 minutes, substantially fully set by 20 minutes. |
| 3 | No setting for 2 minutes, rapid setting 3-6 minutes, substantially fully set by 9 minutes. |
| 4 | No setting for 1 minute, steady setting 2-18 minutes, substantially fully set by 20 minutes. |
| 5 | No setting for 3 minutes, steady setting 4-20 minutes, substantially fully set by 30 minutes. |
| 6 | Friable solid + PVPA → set within 20 seconds. |
| 7 | No setting for 1 minute, steady setting 1-4 minutes, substantially fully set by 6 minutes. |

Part 12

This part describes the preparation of cements from ion-leachable glasses (containing lanthanum or barium ions) and an aqueous solution of PVPA (or PVPA with 5% D2010 hydroxyethyl-diphosphonic acid)). The aqueous acid is a 50% by weight solution of poly(vinyl phosphonic acid) and the cement is made at a powder:-liquid ratio of 3 g:1 ml. The resulting cement-forming reaction is very vigorous, and a hard, dense cement-like mass results in less than 45 seconds. All the cements made with the lanthanum and barium fluoroaluminosilicate glasses were stable in water.

Similar glasses containing strontium instead of barium or lanthanum proved to be very reactive with PVPA. The resulting cements had setting times of only a few seconds. These cements could only be mixed in very low powder:liquid ratios.

The compositions in parts by mass of the different glasses that were used are given below. All these glasses from cements with aqueous PVPA.

| Lanthanum Glasses | | | | | | | |
|---|---|---|---|---|---|---|---|
| Glass | Si:Al | $SiO_2$ | $Al_2O_3$ | $Na_3AlF_6$ | $LaF_3$ | $AlPO_4$ | $AlF_3$ | $CaF_2$ |
| 12A | 1.17 | 176 | 100 | 135 | 146 | 56 | 32 | — |
| 12B | 1.85 | 95 | 100 | 76 | 94 | 73 | — | — |
| 12C | 1.17 | 175 | 100 | — | — | 60 | 32 | 240 |
| 12D | 0.84 | 116 | 66 | — | 33 | 40 | — | 60 |
| 12E | 0.84 | 116 | 66 | — | 60 | 40 | — | 40 |
| 12F | 0.84 | 116 | 66 | — | 100 | 40 | — | 53 |

| Barium Glasses | | | | | | | |
|---|---|---|---|---|---|---|---|
| Glass | Si:Al | $SiO_2$ | $Al_2O_3$ | $Na_3AlF_6$ | $AlPO_4$ | $AlF_3$ | $CaF_2$ | $BaF_2$ |
| 12G | 1.02 | 175 | 100 | 30 | 60 | 32 | 103 | 237 |
| 12H | 1.02 | 175 | 100 | 30 | 60 | 32 | 186 | 47 |

Cements containing lanthanum, barium and strontium glasses have the advantage of increased radio-opacity. Calcium flouroaluminosilicate glass cements are X-ray transparent and are indistinguishable from caries under X-ray conditions. These new cements are visible under X-ray conditions, an important clinical property for materials used to cement crowns. A clinician using X rays to examine a crown would mistake a conventional glass ionomer cement for the caries-dental decay. Materials according to the present invention have a radio-opacity similar to tooth material, and by modifying their composition it may be possible for the clinician to distinguish between tooth and cement under X-ray.

We claim:

1. A cement composition, comprising an intimately blended mixture of a water-containing liquid, a cation-crosslinkable polymeric acid containing on average one phosphonic acid group per one to three backbone carbon atoms, and a cation-leachable surgically acceptable glass powder containing Si and Al in the mol proportions 0.6 to 0.2:1 if previously heat-treated, otherwise exceeding 1.6:1, in the mass proportions (1 minus x) polymeric acid: (1 minus 5) glass: x liquid, where x is from 0.3 to 0.7, said glass containing at least 10% by weight (as the oxide or salt) of a polyvalent metal of atomic number exceeding 37.

2. A cement composition according to claim 1, wherein the glass has been metallised to form a cermet.

3. A cement composition according to claim 1, wherein the glass has been washed in a dilute acid.

4. A cement composition according to claim 1, wherein the glass powder consists of particles all of which are smaller than 100 microns.

5. A cement composition according to claim 1, wherein the glass powder has been heat-treated at at least 400° C. for at least 40 minutes.

6. A cement composition, comprising an intimately blended mixture of a water-containing liquid, a cation-crosslinkable polymeric acid containing on average one phosphonic acid group per one to three backbone carbon atoms, and a metal oxide powder, in the mass proportions (1 minus x) polymeric acid: (1 minus 5) oxide: x liquid, where x is from 0.3 to 0.7, wherein the atomic number of said metal exceeds 37, except Cu, Co, Sn, Bi, Pb, Hg, Cd, Y, La or Mo.

7. A cement composition according to claim 6, wherein the metal oxide is BaO or SrO.

8. A cement composition according to claim 7, wherein the metal oxide has been heat-treated at at least 900° C.

9. A composition according to claim 1, wherein the polymeric acid is or comprises poly(vinyl phosphonic acid).

10. A composition according to claim 9, wherein the polymer acid further comprises poly(acrylic acid).

11. A composition according to claim 1, wherein the liquid is water.

12. A pack comprising two pastes which when mixed form a cement composition according to claim 1.

13. A pack according to claim 12, wherein the first paste contains the acid(s) plus water and the second contains the powder suspended in aqueous thickening agent.

14. A pack comprising the acid(s) in dry form and the powder in the proportions and the compositions of a cement composition according to claim 1.

* * * * *